US012753232B1

(12) United States Patent
Cho et al.

(10) Patent No.: US 12,753,232 B1
(45) Date of Patent: Oct. 6, 2026

(54) FUSION PROTEIN COMPRISING ANTI-CD3 SINGLE DOMAIN ANTIBODY, EXOSOMAL PROTEIN CD63 AND RNA BINDING PROTEIN, AND USES THEREOF

(71) Applicant: China Medical University Hospital, Taichung City (TW)

(72) Inventors: Der-Yang Cho, Taichung City (TW); Shao-Chih Chiu, Taichung City (TW); Shi-Wei Huang, Taichung City (TW); Chih-Ming Pan, Taichung City (TW); Mei-Chih Chen, Taichung City (TW); Yu-Chuan Lin, Taichung City (TW); Yeh Chen, Taichung City (TW); Yi-Wen Chen, Taichung City (TW); Chung-Chun Wu, Taichung City (TW); Kai-Wen Kan, Taichung City (TW)

(73) Assignee: CHINA MEDICAL UNIVERSITY HOSPITAL, Taichung City (TW)

( * ) Notice: Subject to any disclaimer, the term of this patent is extended or adjusted under 35 U.S.C. 154(b) by 0 days.

(21) Appl. No.: 19/433,271

(22) Filed: Dec. 26, 2025

(51) Int. Cl.

| | |
|---|---|
| ***C07K 16/28*** | (2006.01) |
| ***A61K 9/50*** | (2006.01) |
| ***A61P 35/00*** | (2006.01) |
| ***C07K 14/705*** | (2006.01) |
| ***C12N 15/62*** | (2006.01) |
| ***C12N 15/85*** | (2006.01) |
| *A61K 38/00* | (2006.01) |

(52) U.S. Cl.
CPC ........ *C07K 16/2809* (2013.01); *A61K 9/5068* (2013.01); *A61P 35/00* (2018.01); *C07K 14/70539* (2013.01); *C07K 14/70596* (2013.01); *C12N 15/62* (2013.01); *C12N 15/85* (2013.01); *A61K 38/00* (2013.01); *C07K 2317/569* (2013.01); *C07K 2319/85* (2013.01)

(58) Field of Classification Search
CPC .................................................. C07K 16/2809
USPC ....................................................... 424/134.1
See application file for complete search history.

(56) References Cited

U.S. PATENT DOCUMENTS

2016/0137716 A1* 5/2016 El Andaloussi ........ A61P 17/00 435/375
2022/0306748 A1* 9/2022 Cho .................. C07K 16/2833
2023/0203532 A1 6/2023 Iikow et al.

FOREIGN PATENT DOCUMENTS

EP 4596583 A1 8/2025
WO WO2019027847 A1 2/2019
WO WO2020205579 A1 10/2020
WO WO 2021/102585 A1 * 6/2021

OTHER PUBLICATIONS

Long et al (Journal of Hematology & Oncology, 2024, 17(20): 1-17).*
Slotwinski et al (Centr Eur J Immunol, 2018, 43(3): 314-324).*
Uddin et al (Cancers, 2021, 13(2777): 1-19).*
Villarroya-Beltri et al (Nature Communications, 2013, 4(2980): 1-10).*
Kozu et al (Genomics, 1995, 25: 365-371).*
Jan et al (J Immunother Cancer, 2021, 9(e003050): 1-16).*
Extended European Search Report for European Patent Application No. 26156838.0 dated Jul. 15, 2026.
Gurrieri Elena et al: “Strategies to functionalize extracellular vesicles against HER2 for anticancer activity”, Extracellular Vesicles and Circulating Nucleic Acids, vol. 3, No. 2, Jan. 1, 2022 (Jan. 1, 2022), pp. 93-101, XP093412438, ISSN: 2767-6641, DOI: 10.20517/evcna.2022.07.
Si Ke et al: “Engineering exosome-mediated messenger RNA and single-chain variable fragment delivery for human chimeric antigen receptor T-cell engineering”, Cytotherapy, vol. 25, No. 6, Jun. 1, 2023 (Jun. 1, 2023), pp. 615-624, XP09319992, GB ISSN: 1465-3249, DOI: 10.1016/j.jcyt.2023.01.005.
Cheng Qinqin et al: “Reprogramming Exosomes as Nanoscale Controllers of Cellular Immunity”, Journal of the American Chemical Society, vol. 140, No. 48, Nov. 19, 2018 (Nov. 19, 2018), pp. 16413-16417, XP055786115, DOI: 10.1021/jacs.8b10047.

* cited by examiner

*Primary Examiner* — Sean E Aeder
(74) *Attorney, Agent, or Firm* — WPAT, PC

(57) ABSTRACT

The present disclosure provides a fusion protein including an anti-CD3 single domain antibody, an exosomal protein CD63 and an RNA binding protein. The fusion protein of the present disclosure achieves the effect of treating cancer, immunoregulation and activating immune cells through various efficacy experiments.

18 Claims, 16 Drawing Sheets

Specification includes a Sequence Listing.

FUSION PROTEIN COMPRISING ANTI-CD3 SINGLE DOMAIN ANTIBODY, EXOSOMAL PROTEIN CD63 AND RNA BINDING PROTEIN, AND USES THEREOF

STATEMENT REGARDING SEQUENCE LISTING

The sequence listing associated with this application is provided in text format in lieu of a paper copy and is hereby incorporated by reference into the specification. The name of the XML file containing the sequence listing is 114F0420-IE_Sequence_listing. The XML file is 9000 bytes; was created on Sep. 25, 2025.

BACKGROUND OF THE INVENTION

1. Field of the Invention

The present invention relates to a fusion protein comprising an anti-CD3 single domain antibody, an exosomal protein CD63 and an RNA binding protein, and uses thereof.

2. The Prior Art

Cancer, also known as malignancy, is a state of abnormal proliferation of cells, and these proliferating cells may invade other parts of the body as a disease caused by a malfunction in the control of cell division and proliferation. The number of people suffering from cancer worldwide has a growing trend. Cancer is one of the top ten causes of death for the Chinese people and has been the top ten causes of death for consecutive years.

Conventional cancer treatments include surgery, radiation therapy, chemotherapy, and target therapy. Cancer immunotherapy is another method for treating cancer except the above methods. The immune system of the patient is activated in the cancer immunotherapy by using tumor cells or tumor antigens to induce specific cellular and humoral immune responses for enhancing the anti-cancer ability of the patient, preventing the growth, spread, and recurrence of tumors, and achieving the purpose of removing or controlling tumors. However, the current tumor treatments still have the problems of ineffectiveness and strong side effects, and even lead to other immune-related disorders.

CD3ε (CD3 epsilon), a transmembrane protein found on T cells, has been found to be associated with tumors and regulation of immune function. Therefore, researchers have been committed to developing CD3ε as target molecules for tumor identification and regulation of immune function and to find out whether these target molecules have the potential to become anticancer drugs or immunoregulatory drugs. In addition, CD63 is a protein antigen encoded by the CD63 gene in humans. CD63 mainly appears on the surface of extracellular vesicles and also on the surface of ordinary cell membranes. Its encoding gene is related to tumor development.

In order to solve the above-mentioned problems, those skilled in the art urgently need to develop a novel and effective medicament for treating cancer, immunoregulation and activating immune cells for the benefit of a large group of people in need thereof.

SUMMARY OF THE INVENTION

A primary objective of the present invention is to provide a fusion protein, comprising an anti-CD3 single domain antibody, an exosomal protein, and an RNA binding protein, wherein the amino acid sequence of the anti-CD3 single domain antibody is heavy chain variable domain (VHH), and the exosomal protein is CD63.

Another objective of the present invention is to provide a pharmaceutical composition, comprising the abovementioned fusion protein and a pharmaceutically acceptable carrier.

According to an embodiment of the present invention, the anti-CD3 single domain antibody specifically binds to a CD3 ε.

According to an embodiment of the present invention, the anti-CD3 single domain antibody is an anti-T cell nanobody.

According to an embodiment of the present invention, the anti-CD3 single domain antibody comprises an amino acid sequence of SEQ ID NO:2.

According to an embodiment of the present invention, the amino acid sequence of N-terminus of the CD63 is SEQ ID NO:3, and the amino acid sequence of C-terminus of the CD63 is SEQ ID NO:4.

According to an embodiment of the present invention, the RNA binding protein is heterogeneous nuclear ribonucleoprotein (hnRNP) A2B1.

According to an embodiment of the present invention, the hnRNP A2B1 comprises an amino acid sequence of SEQ ID NO:5.

According to an embodiment of the present invention, the fusion protein comprises an amino acid sequence of SEQ ID NO:1.

According to an embodiment of the present invention, the fusion protein further comprises an extracellular vesicle (EV) sorting motif.

According to an embodiment of the present invention, the nucleotide sequence encoding the amino acid sequence of the EV sorting motif is SEQ ID NO:6.

According to an embodiment of the present invention, the fusion protein further comprises an HLA-G chimeric antigen receptor (CAR).

Another objective of the present invention is to provide a method for treating cancer, immunoregulation and activating immune cells, comprising administering to a subject in need thereof the abovementioned pharmaceutical composition.

According to an embodiment of the present invention, the fusion protein enhances anti-tumor activity of peripheral blood mononuclear cells (PBMCs).

According to an embodiment of the present invention, the cancer is colorectal cancer, lung adenocarcinoma, glioblastoma, or pancreatic cancer.

In summary, the fusion protein of the present invention achieves the effect of treating cancer, immunoregulation and activating immune cells through the results illustrated in the following examples.

The embodiments of the present invention would be further described below. The following examples are used to illustrate the present invention and are not intended to limit the scope of the present invention. Anyone skilled in the art can make some changes and modifications without departing from the spirit and scope of the present invention. Therefore, the scope of the present invention shall be defined by the appended claims.

BRIEF DESCRIPTION OF THE DRAWINGS

The following drawings form part of the present specification and are included here to further demonstrate some aspects of the present invention, which can be better understood by reference to one or more of these drawings, in combination with the detailed description of the embodiments presented herein.

Figure 1A:
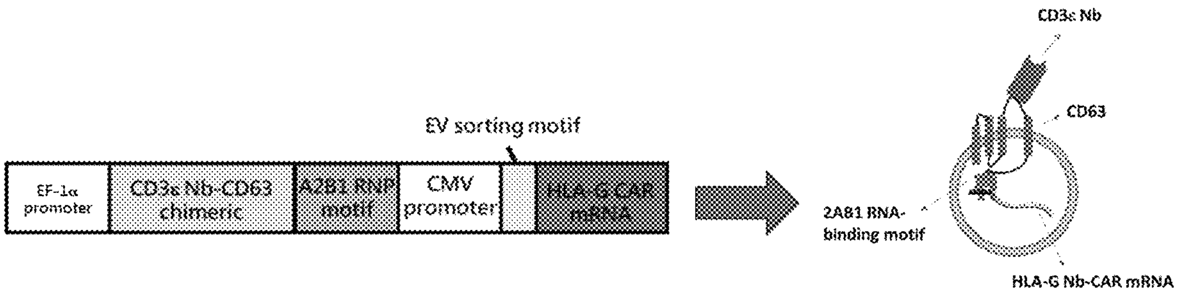
FIGS. 1A-1E show characterization of the fusion protein, in which the fusion protein is also called preloaded CD3ε-nanobody (Nb) extracellular vesicles (EVs) (preload CD3ε-Nb EVs). (1A) Schematic representation of preload CD3ε-Nb EV construct, in which EF-1α promoter represents elongation factor-1 alpha promoter, CMV promoter represents Cytomegalovirus promoter, RNP motif represents ribonucleoprotein motif, EV sorting motif represents extracellular vesicle sorting motif, CAR represents chimeric antigen receptor, CD3 ε Nb represents the anti-CD3 single domain antibody. The first EF-1α promoter drive a CD3ε nanobody (Nb)-CD63 chimeric construct which consists of the exosome tetraspanin protein CD63, with a CD3 ε Nb inserted into the extracellular loop between the third and fourth transmembrane domains, followed a RNA recognition motif (RRM) incept from heterogeneous nuclear ribonucleoprotein A2B1 (hnRNPA2B1). Subsequently fused with secondary EF-1α promoter to drive a HLA-G Nb-CAR construct containing a EV sorting motif derived from miR198. The vector was transfected into HEK-293T cells for producing HLA-G Nb-CAR mRNA-enriched CD3ε-Nb extracellular vesicles (preload CD3ε-Nb EVs as short) (1B, 1C). The particle size distributions of parental and preload CD3ε-Nb EVs were determined by nanoparticle tracking analysis (NTA) (1B), and the expression levels of heavy chain variable domain (VHH), CD63, TSG101 and β-actin were detected by dot plot using specific antibodies (1C). (1D, 1E). Protocol for determining the contents of HLA-G Nb-CAR mRNA in HEK-293T-derived EVs. Parental and preload CD3ε-Nb EVs were incubated with bead-conjugated anti-VHH antibody, then isolated the fractions of EVs by magnetic system. Subsequently, the EV fractions were subjected into qPCR analysis using specific Taqman primers of HLA-G Nb-CAR mRNA (1D).
Figure 1B:
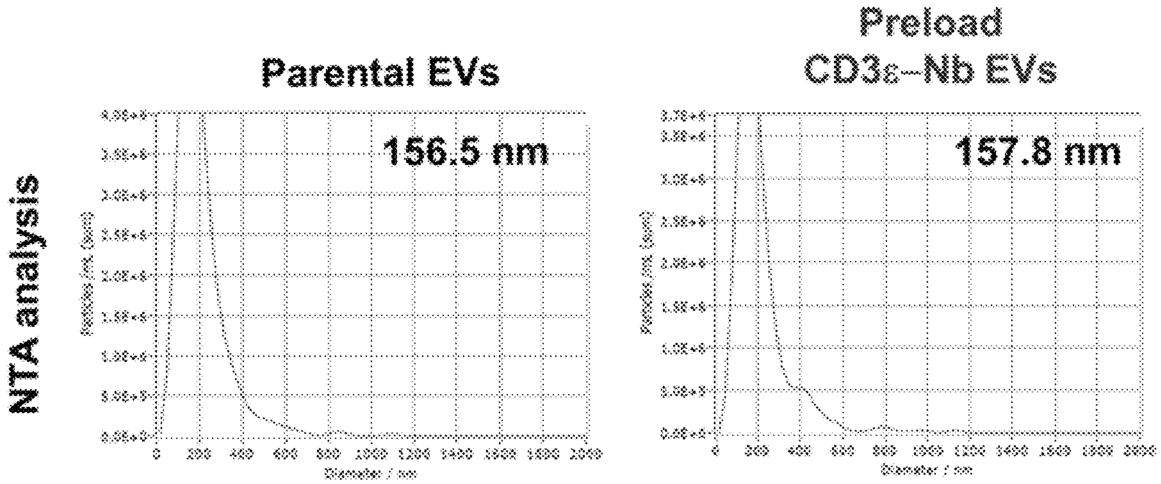
Figure 1C:
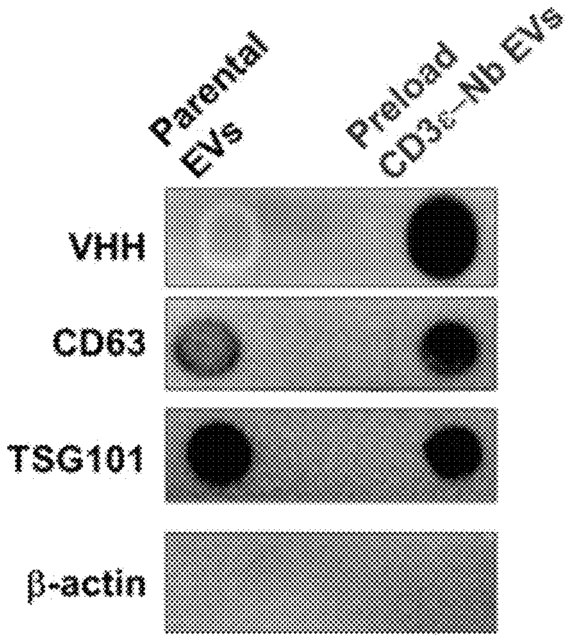
Figure 1D:
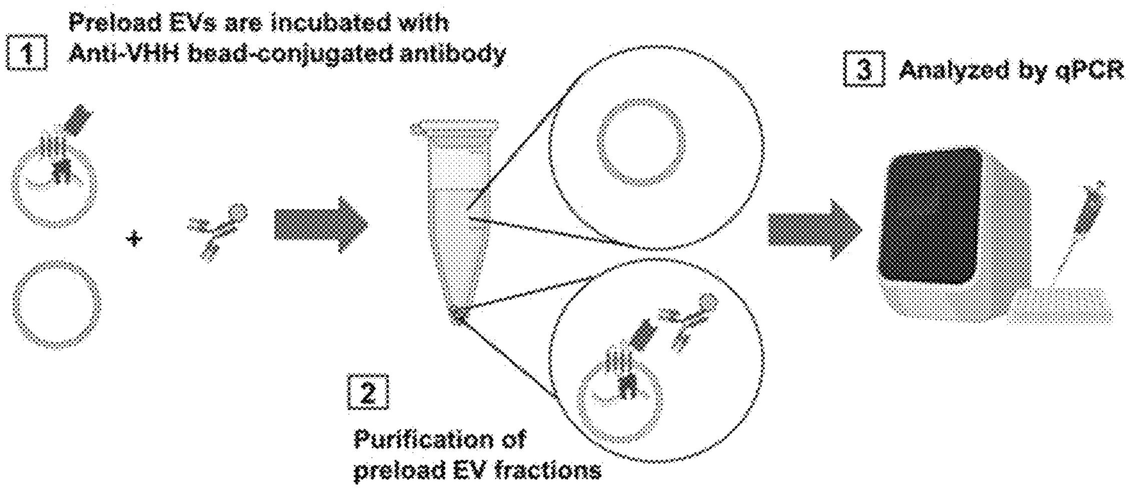
Figure 1E:
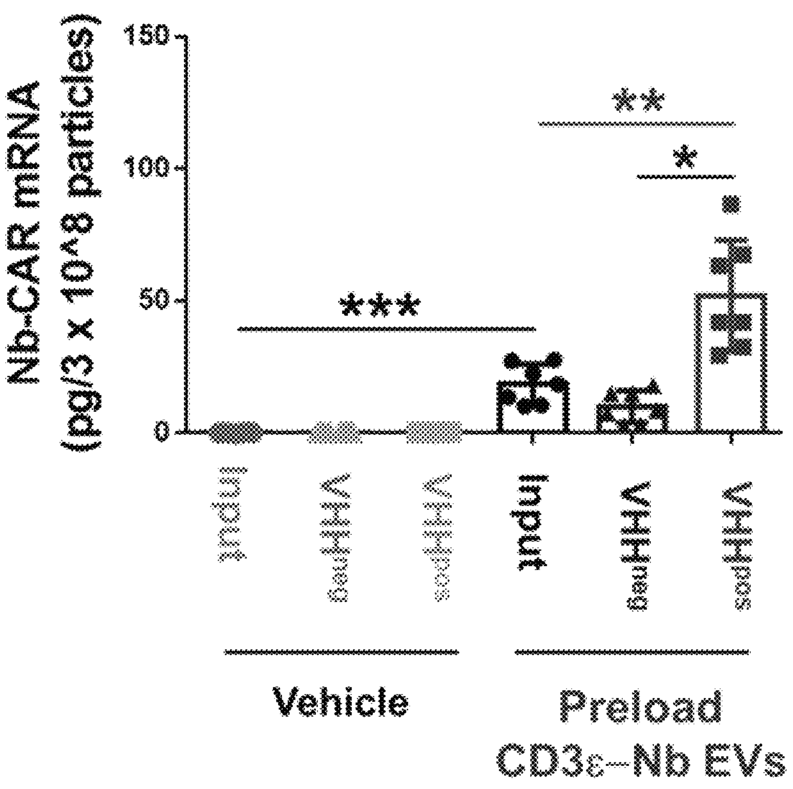

Schematic protocol for evaluating antitumor activity of I.M. injection of preload CD3ε-Nb EV transgene in COLO 205 tumor-bearing PBMC-humanized NSG mice (huNSG). After 7 days of intraperitoneally (I.P.) implanted with COLO 205 tumor cells (1×10^6 cells), the mice were infused with 5×10^6 PBMCs through tail vein. On the next day, the mice were I.M. injected with or without preload CD3ε-Nb EV DNA transgene (1 mg/kg) at the right hind leg. The tumor growth rates were monitored by IVIS imaging system through bioluminescent channel (9B, 9C), and their survival rates were recorded (9D).

DETAILED DESCRIPTION OF THE PREFERRED EMBODIMENT

In the following detailed description of the embodiments of the present invention, reference is made to the accompanying drawings, which are shown to illustrate the specific embodiments in which the present disclosure may be practiced. These embodiments are provided to enable those skilled in the art to practice the present disclosure. It is understood that other embodiments may be used and that changes can be made to the embodiments without departing from the scope of the present invention. The following description is therefore not to be considered as limiting the scope of the present invention.

Definition

As used herein, the data provided represent experimental values that can vary within a range of ±20%, preferably within ±10%, and most preferably within ±5%.

Unless otherwise stated in the context, "a", "the" and similar terms used in the specification (especially in the following claims) should be understood as including singular and plural forms.

As used herein, the terms "CD3ε" and "CD3 ε" can be used interchangeably.

As used herein, the terms "CD3e nanobody", "CD3e nb", "CD3e Nb", "CD3e nanobody", "anti-CD3ε nanobody", "anti-CD3 single domain antibody", and "anti-T cell nanobody" can be used interchangeably.

As used herein, the term "treating" or "treatment" refers to alleviating, reducing, ameliorating, relieving or controlling one or more clinical signs of a disease or disorder, and lowering, stopping, or reversing the progression of severity regarding the condition or symptom being treated.

According to the present invention, the pharmaceutical composition can be manufactured to a dosage form suitable for parenteral administration, using techniques well known to those skilled in the art, including, but not limited to, injection (e.g., sterile aqueous solution or dispersion), sterile powder, tablet, troche, lozenge, pill, capsule, dispersible powder or granule, solution, suspension, emulsion, syrup, elixir, slurry, and the like.

The pharmaceutical composition according to the present invention may be administered by a parenteral route selected from the group consisting of: intraperitoneal injection, subcutaneous injection, intraepidermal injection, intradermal injection, intramuscular injection, intravenous injection, and intralesional injection.

According to the present invention, the pharmaceutical composition may further comprise a pharmaceutically acceptable carrier which is widely used in pharmaceutically manufacturing techniques. For example, the pharmaceutically acceptable carrier can comprise one or more reagents selected from the group consisting of solvent, emulsifier, suspending agent, decomposer, binding agent, excipient, stabilizing agent, chelating agent, diluent, gelling agent, preservative, lubricant, absorption delaying agent, liposome, and the like. The selection and quantity of these reagents fall within the scope of the professional literacy and routine techniques of those skilled in the art.

According to the present invention, the pharmaceutically acceptable carrier comprises a solvent selected from the group consisting of water, normal saline, phosphate buffered saline (PBS), sugar-containing solution, aqueous solution containing alcohol, and combinations thereof.

As used herein, the term "nucleic acid", "nucleic acid sequence" or "nucleic acid fragment" refers to a sequence of deoxyribonucleotides or ribonucleotides in single- or double-stranded forms, and comprises known naturally occurring nucleotides or artificially chemical mimics. As used herein, the term "nucleic acid" is used interchangeably with the terms "gene", "cDNA", "mRNA", "oligonucleotide" and "polynucleotide".

According to the present invention, the amino acid sequence of the fusion protein is SEQ ID NO: 1. The fusion protein comprises an anti-CD3 single domain antibody, and the amino acid sequence of the anti-CD3 single domain antibody is SEQ ID NO:2. The amino acid sequence of the anti-CD3 single domain antibody is heavy chain variable domain (VHH).

According to the present invention, the fusion protein comprises an exosomal protein CD63, the amino acid sequence of the N-terminus of the exosomal protein CD63 is SEQ ID NO:3, and the amino acid sequence of the C-terminus of the exosomal protein CD63 is SEQ ID NO:4.

According to the present invention, the fusion protein comprises an RNA binding protein, wherein the RNA binding protein is heterogeneous nuclear ribonucleoprotein (hnRNP) A2B1. The amino acid sequence of the hnRNP A2B1 is SEQ ID NO:5.

According to the present invention, the fusion protein can comprise an extracellular vesicle (EV) sorting motif. The nucleotide sequence encoding the amino acid sequence of the EV sorting motif is SEQ ID NO:6.

According to the present invention, the fusion protein can comprise an HLA-G chimeric antigen receptor (CAR).

According to the present invention, the fusion protein can comprise a linker. The amino acid sequence of the linker is SEQ ID NO:7.

According to the present invention, the anti-CD3 single domain antibody specifically binds to a CD3 ε.

According to the present invention, the anti-CD3 single domain antibody is an anti-T cell nanobody.

The present invention is further illustrated by the following examples. These examples are provided for illustration only and are not intended to limit the scope of the present invention. The scope of the present invention is shown in the appended claims.

Example 1

Characterization of Fusion Protein of Present Invention

FIGS. 1A-1E show characterization of the fusion protein, in which the fusion protein is also called preloaded CD3ε-nanobody (Nb) extracellular vesicles (EVs) (preload CD3ε-Nb EVs). (1A) Schematic representation of preload CD3ε-Nb EV construct, in which Er-1α promoter represents elongation factor-1 alpha promoter, CMV promoter represents Cytomegalovirus promoter, RNP motif represents ribonucleoprotein motif, EV sorting motif represents extracellular vesicle sorting motif, CAR represents chimeric antigen receptor, CD3 ε Nb represents the anti-CD3 single domain antibody. The first EF-1α promoter drive a CD3ε nanobody (Nb)-CD63 chimeric construct which consists of the exosome tetraspanin protein CD63, with a CD3ε Nb inserted into the extracellular loop between the third and fourth transmembrane domains, followed a RNA recognition motif (RRM) incept from heterogeneous nuclear ribonucleoprotein A2B1 (hnRNPA2B1). Subsequently fused with secondary EF-1α promoter to drive a HLA-G Nb-CAR construct containing a EV sorting motif derived from miR198. The vector was transfected into HEK-293T cells for producing HLA-G Nb-CAR mRNA-enriched CD3ε-Nb extracellular vesicles (preload CD3ε-Nb EVs as short) (1B, 1C). The particle size distributions of parental and preload CD3ε-Nb EVs were determined by nanoparticle tracking analysis (NTA) (1B), and the expression levels of heavy chain variable domain (VHH), CD63, TSG101 and β-actin were detected by dot plot using specific antibodies (1C). (1D, 1E). Protocol for determining the contents of HLA-G Nb-CAR mRNA in HEK-293T-derived EVs. Parental and preload CD3ε-Nb EVs were incubated with bead-conjugated anti-VHH antibody, then isolated the fractions of EVs by magnetic system. Subsequently, the EV fractions were subjected into qPCR analysis using specific Taqman primers of HLA-G Nb-CAR mRNA (1D).

Based on the results of FIGS. 1A-1E, the fusion protein of the present invention was obtained and its characteristics were determined. The fusion protein was then used to perform the following experiments.

Example 2

Transfection Efficiency of Fusion Protein of Present Invention In Vitro

Figure 2A:
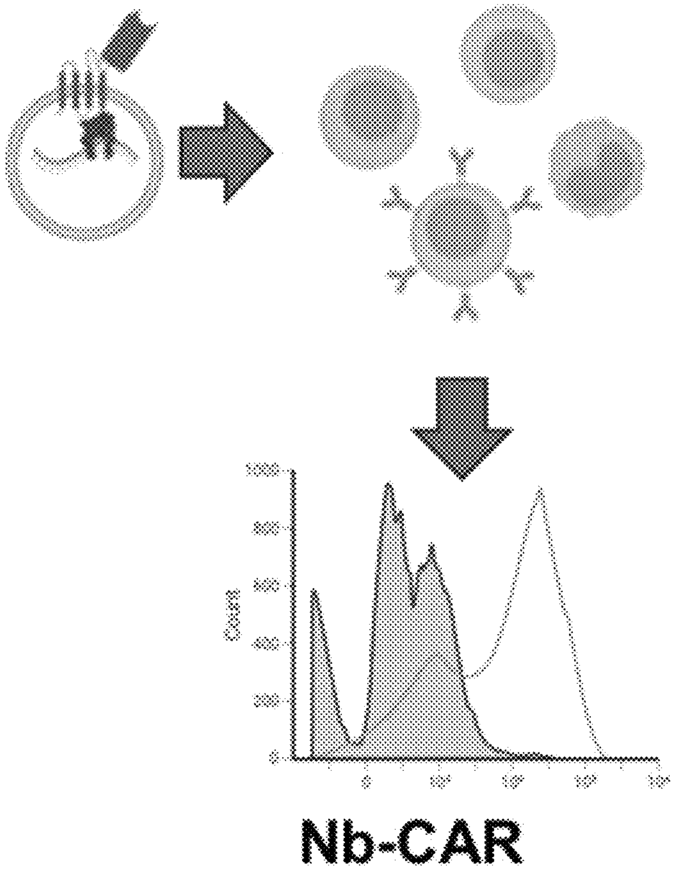
FIGS. 2A and 2B show the transfection efficiency of the fusion protein in vitro, in which the fusion protein is also called preloaded CD3ε-nanobody (Nb) extracellular vesicles (EVs) (preload CD3ε-Nb EVs). (2A) Schematic protocol of transfection efficiency of preload CD3ε-Nb EV construct. After one day of control and preload CD3e-Nb EV (2×10ˆ9 particles) treatment, the peripheral blood mononuclear cells (PBMCs) were harvested and determined the expression levels of Nb-CAR on $CD3^+$ and $CD3^-$ cells through flow cytometry analysis using specific antibodies against VHH and CD3 (2B).
Figure 2B:
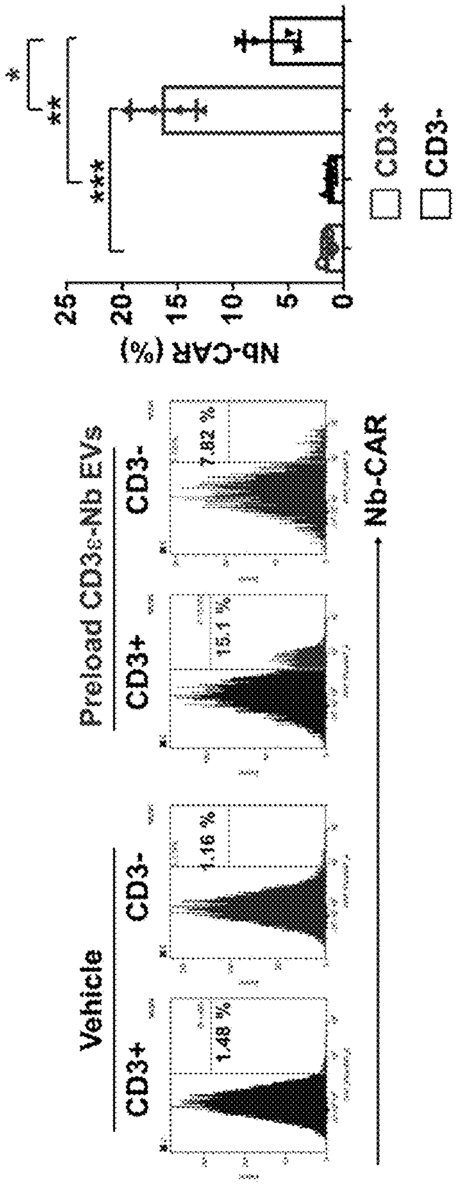

FIGS. 2A and 2B show the transfection efficiency of the fusion protein in vitro, in which the fusion protein is also called preloaded CD3ε-nanobody (Nb) extracellular vesicles (EVs) (preload CD3ε-Nb EVs). (2A) Schematic protocol of transfection efficiency of preload CD3ε-Nb EV construct. After one day of control and preload CD3e-Nb EV (2×10^9 particles) treatment, the peripheral blood mononuclear cells (PBMCs) were harvested and determined the expression levels of Nb-CAR on $CD3^+$ and $CD3^-$ cells through flow cytometry analysis using specific antibodies against VHH and CD3 (2B).

Example 3

Anti-Tumor Activity of PBMCs were Enhanced by Treating Fusion Protein In Vitro

Figure 3:
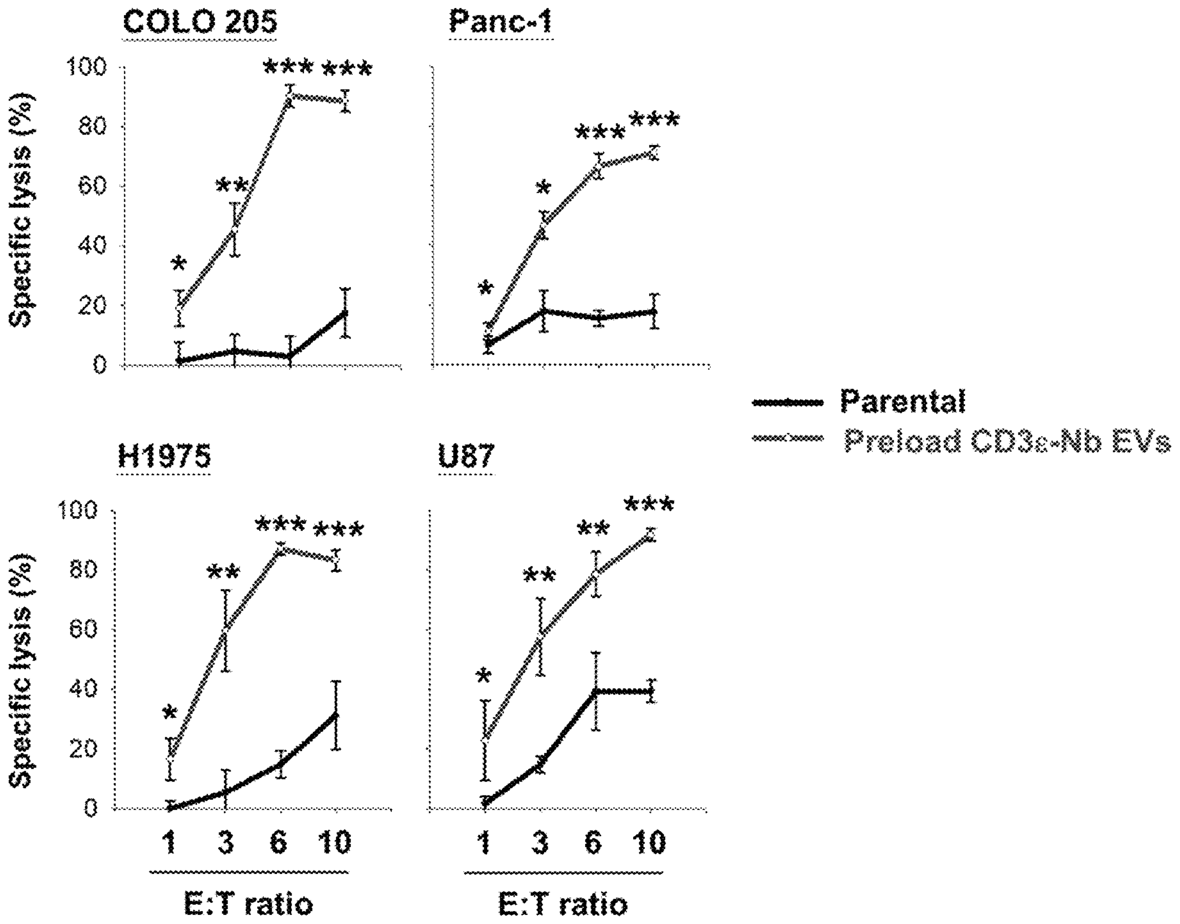
FIG. 3 shows that anti-tumor activity of PBMCs were enhanced by treating the fusion protein in vitro, in which the fusion protein is also called preloaded CD3ε-nanobody (Nb) extracellular vesicles (EVs) (preload CD3ε-Nb EVs). After one day of control and preload CD3ε-Nb EV (2×10ˆ9 particles) treatment, the PBMCs subjected to co-culture with COL0205 (human colorectal cancer cell line), H1975 (human lung adenocarcinoma cell line), U87 (human glioblastoma cell line) and Panc-1 (human pancreatic cancer cell line) cells at effector-to-target (E:T) ratios as 1:1, 3:1, 6:1 and 10:1. The induced cytotoxicity was determined by LIVE/DEAD Cell-Mediated Cytotoxicity Assay kit using flow cytometry analysis according to the user's instruction.

FIG. 3 shows that anti-tumor activity of PBMCs were enhanced by treating the fusion protein in vitro, in which the fusion protein is also called preloaded CD3ε-nanobody (Nb) extracellular vesicles (EVs) (preload CD3ε-Nb EVs). After one day of control and preload CD3ε-Nb EV (2×10^9 particles) treatment, the PBMCs subjected to co-culture with COL0205 (human colorectal cancer cell line), H1975 (human lung adenocarcinoma cell line), U87 (human glioblastoma cell line) and Panc-1 (human pancreatic cancer cell line) cells at effector-to-target (E:T) ratios as 1:1, 3:1, 6:1 and 10:1. The induced cytotoxicity was determined by LIVE/DEAD Cell-Mediated Cytotoxicity Assay kit using flow cytometry analysis according to the user's instruction.

The results of this example indicate that anti-tumor activity of PBMCs were enhanced by treating the fusion protein in vitro.

Example 4

Transfection Efficiency of Fusion Protein of Present Invention In Vivo

Figure 4A:
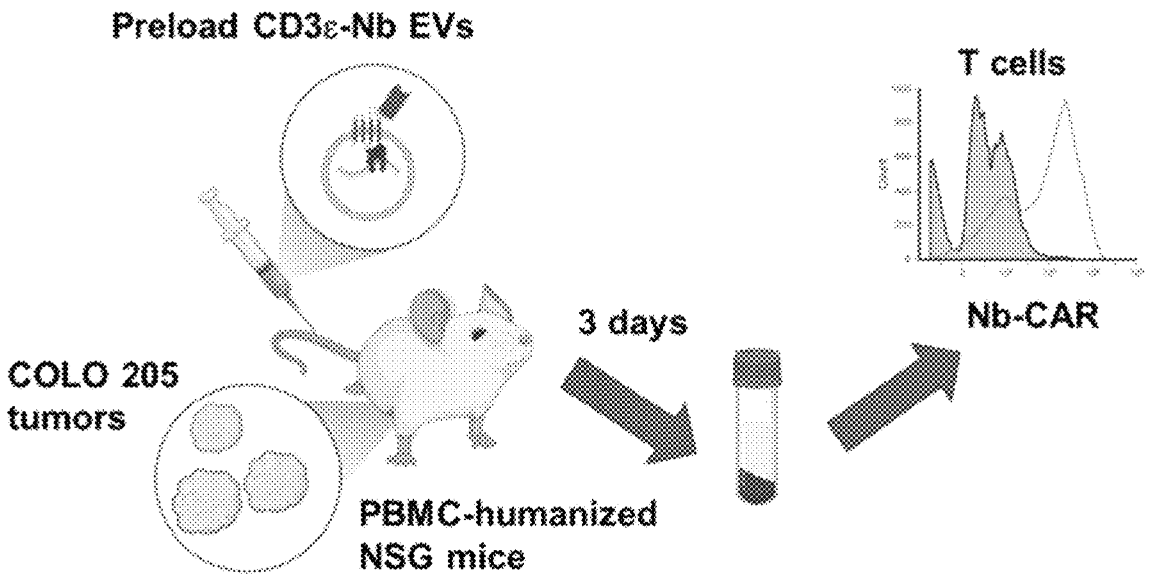
FIGS. 4A and 4B show the transfection efficiency of the fusion protein in vivo, in which the fusion protein is also called preloaded CD3ε-nanobody (Nb) extracellular vesicles (EVs) (preload CD3ε-Nb EVs). (4A) Schematic protocol of transfection efficiency of preload CD3ε-Nb EVs in COLO 205 tumor-bearing PBMC-humanized NSG mice (huNSG). After 3 days of control or preload CD3ε-Nb EVs (1×10ˆ10 particles) infusion, the buffy coats were harvested from the mice, and determined the expression levels of Nb-CAR on $CD3^+$ and $CD3^-$ cells through flow cytometry analysis using specific antibodies against VHH and CD3 (4B).
Figure 4B:
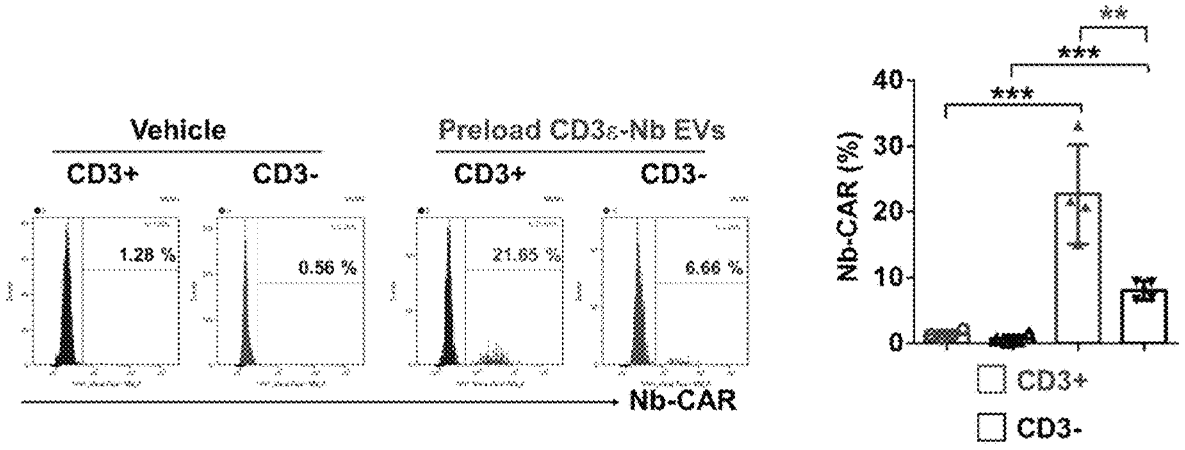
Figure 5A:
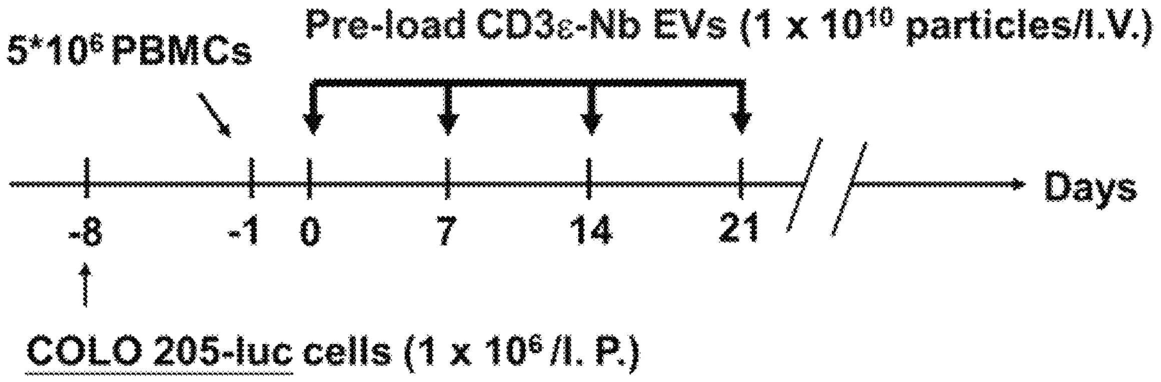
FIGS. 5A-5D show antitumor efficiency of the fusion protein in vivo, in which the fusion protein is also called preloaded CD3ε-nanobody (Nb) extracellular vesicles (EVs) (preload CD3ε-Nb EVs). (5A) Schematic protocol for evaluating antitumor efficiency of preload CD3ε-Nb EVs in COLO 205 tumor-bearing PBMC-humanized NSG mice (huNSG). After 7 days of COLO 205 tumor cells implantation (1×10ˆ6 cells/intraperitoneal injection (I.P.)), the mice were tail vein injected with 5×10ˆ6 PBMCs. On the next day, the mice were infused with or without preload CD3ε-Nb EVs (1×10ˆ10 particles) once a week for four weeks. The tumor growth rates were monitored by in vitro imaging system (IVIS) using bioluminescent channel (5B, 5C), and their survival rate was recorded (5D).
Figure 5B:
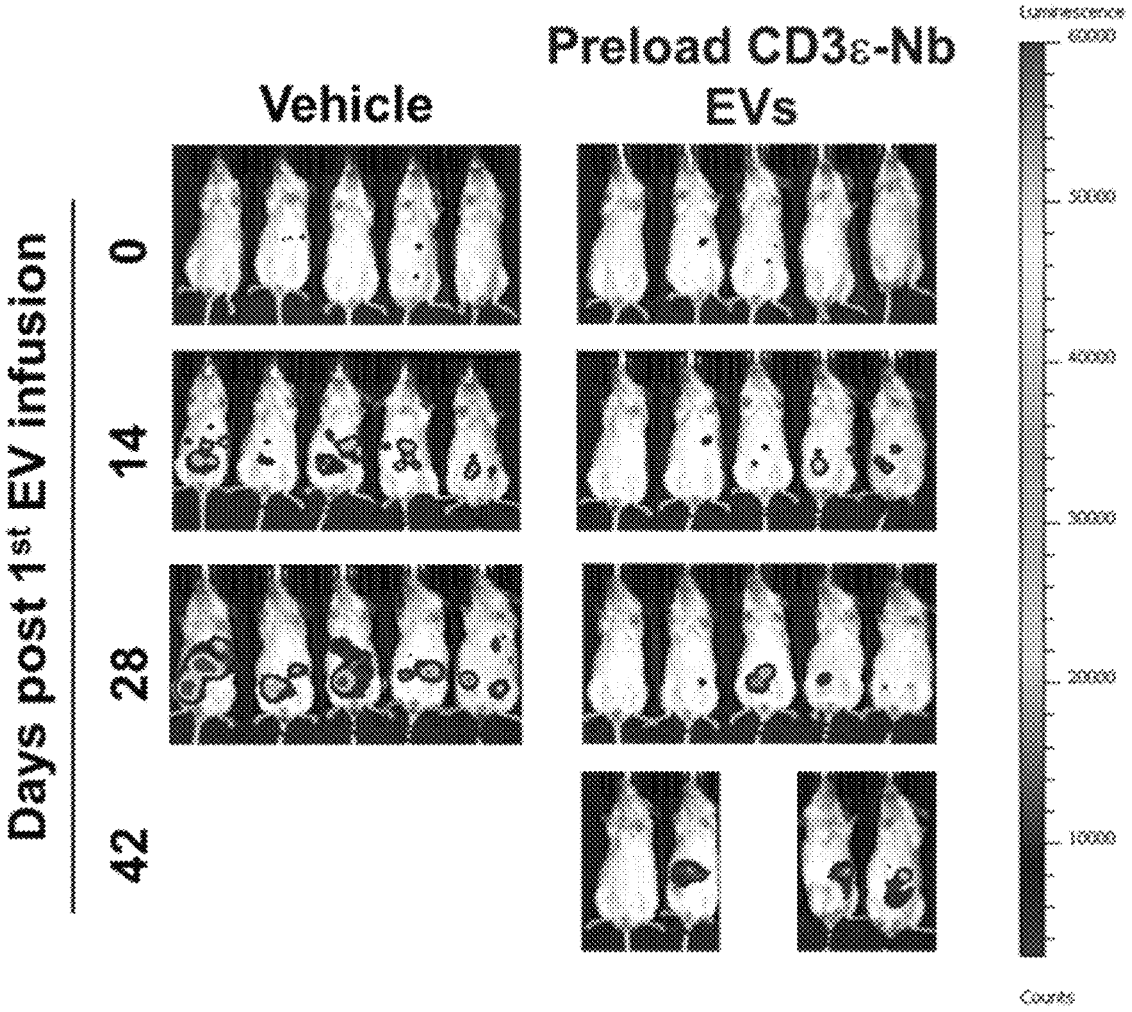
Figure 5C:
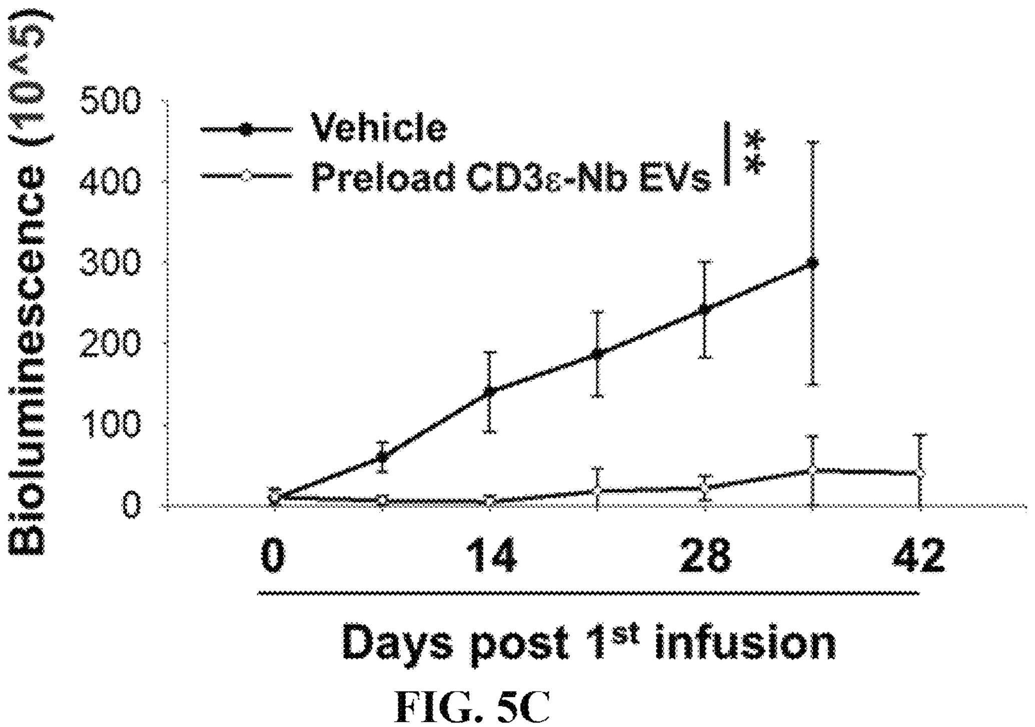
Figure 5D:
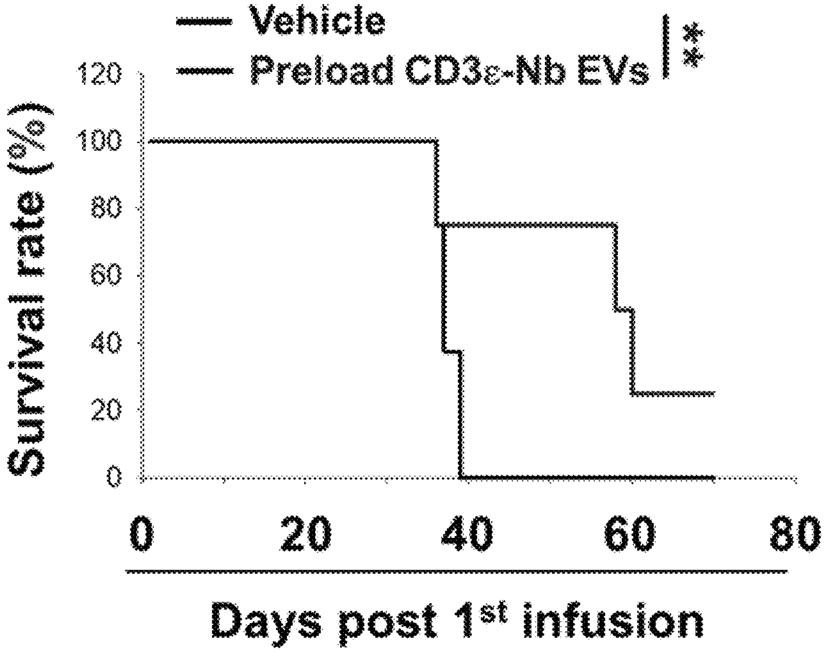

FIGS. 4A and 4B show the transfection efficiency of the fusion protein in vivo, in which the fusion protein is also called preloaded CD3ε-nanobody (Nb) extracellular vesicles (EVs) (preload CD3ε-Nb EVs). (4A) Schematic protocol of transfection efficiency of preload CD3ε-Nb EVs in COLO 205 tumor-bearing PBMC-humanized NSG mice (huNSG). After 3 days of control or preload CD3ε-Nb EVs (1×10^10 particles) infusion, the buffy coats were harvested from the mice, and determined the expression levels of Nb-CAR on $CD3^+$ and $CD3^-$ cells through flow cytometry analysis using specific antibodies against VHH and CD3 (4B).

Example 5

Treatment of Fusion Protein Enhances Anti-Tumor Activity Against Solid Tumor In Vivo FIGS. 5A-5D show antitumor efficiency of the fusion protein in vivo, in which the fusion protein is also called preloaded CD3ε-nanobody (Nb) extracellular vesicles (EVs) (preload CD3ε-Nb EVs). (5A) Schematic protocol for evaluating antitumor efficiency of preload CD3ε-Nb EVs in COLO 205 tumor-bearing PBMC-humanized NSG mice (huNSG). After 7 days of COLO 205 tumor cells implantation (1×10^6 cells/intraperitoneal injection (I.P.)), the mice were tail vein injected with 5×10^6 PBMCs. On the next day, the mice were infused with or without preload CD3ε-Nb EVs (1×10^10 particles) once a week for four weeks. The tumor growth rates were monitored by in vitro imaging system (IVIS) using bioluminescent channel (5B, 5C), and their survival rate was recorded (5D).

The results of this example indicate that treatment of the fusion protein enhances anti-tumor activity against solid tumor in vivo.

Example 6

Figure 6A:
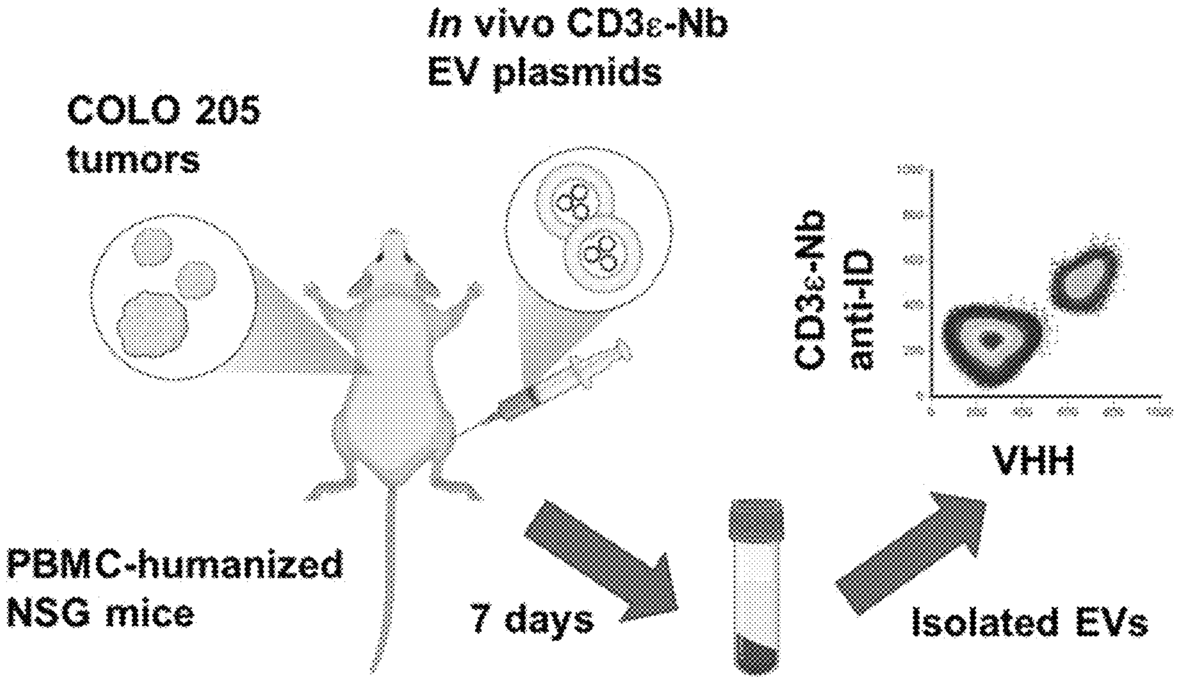
FIGS. 6A and 6B show in vivo generation of the fusion protein, in which the fusion protein is also called preloaded CD3ε-nanobody (Nb) extracellular vesicles (EVs) (preload CD3ε-Nb EVs). (6A) Schematic protocol for in vivo generation of preload CD3ε-Nb EVs in COLO 205 tumor-bearing PBMC-humanized NSG mice (huNSG). After 7 days of intramuscular (I.M.) injection with vehicle control or preload CD3ε-Nb EV DNA transgene (1 mg/kg) at the right hind leg, the plasma were harvested from the mice, and determined the expression levels of CD3ε Nb moieties on EV particles through flow cytometry analysis using specific antibodies against VHH and CD3ε Nb, and the defined beads for size determination (6B).
Figure 6B:
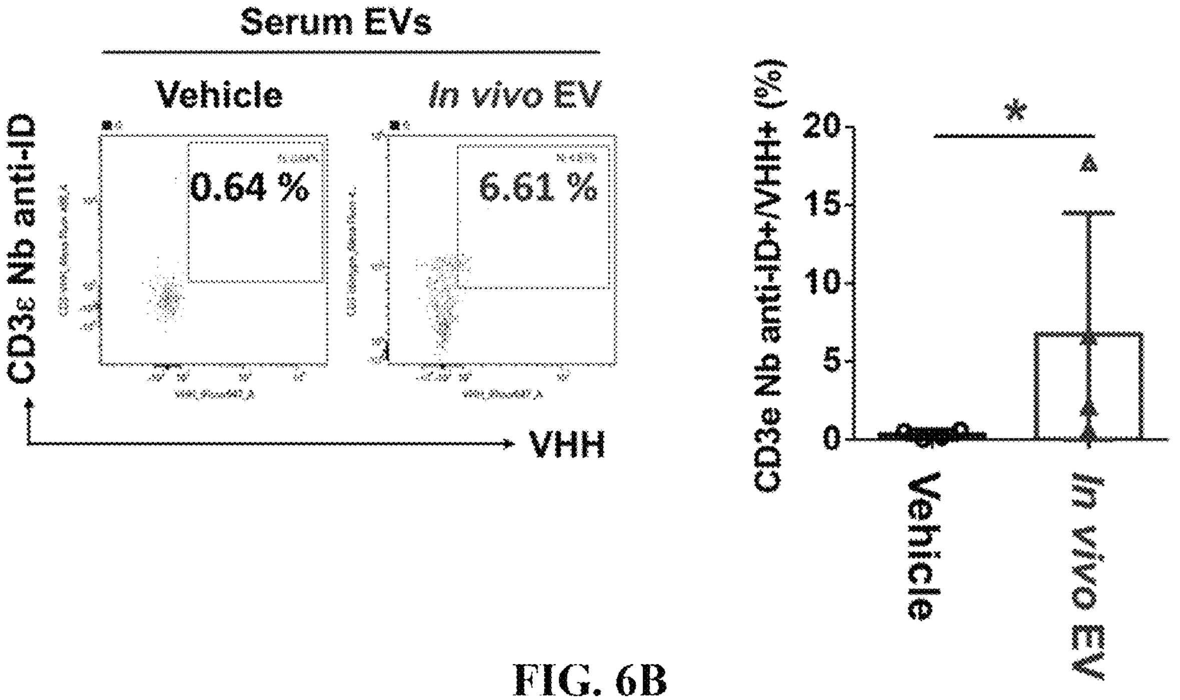
Figure 7A:
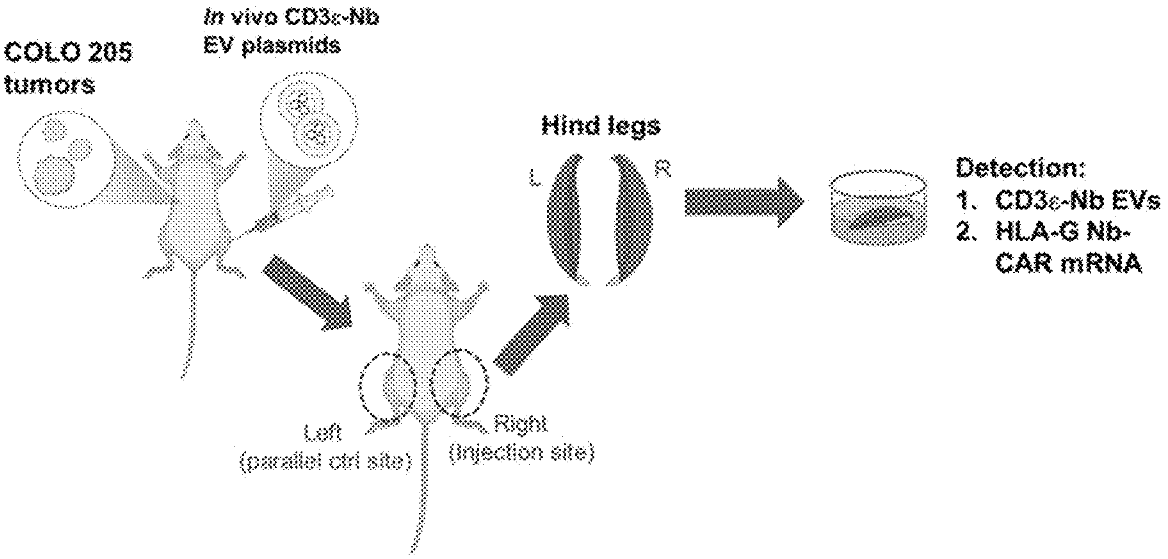
FIGS. 7A-7D show demonstration of in vivo generated the fusion protein from hind leg through intramuscular injection route, in which the fusion protein is also called preloaded CD3ε-nanobody (Nb) extracellular vesicles (EVs) (preload CD3ε-Nb EVs). (7A) After 7 days of I.M. injection with vehicle control or preload CD3ε-Nb EV DNA transgene (1 mg/kg) at the right hind leg, the mice were sacrificed and their muscle tissues of both hind legs were collected. Subsequently, these hind leg tissues were subjected into 6-well plate supplemented with 1 ml serum-free RPMI1640 media. On the next day, the supernatants were harvested and filtrated with 0.22 μm filter membrane and 30 kDa cut-off column. Then the purified supernatants were analyzed by dot plot (7B) or flow cytometry analysis using specific antibodies against VHH and CD3ε Nb, and the defined beads for size determination (7C), or the levels of HLA-G Nb-CAR mRNA was detected by qPCR using specific Taqman primer probe (7D).
Figure 7B:
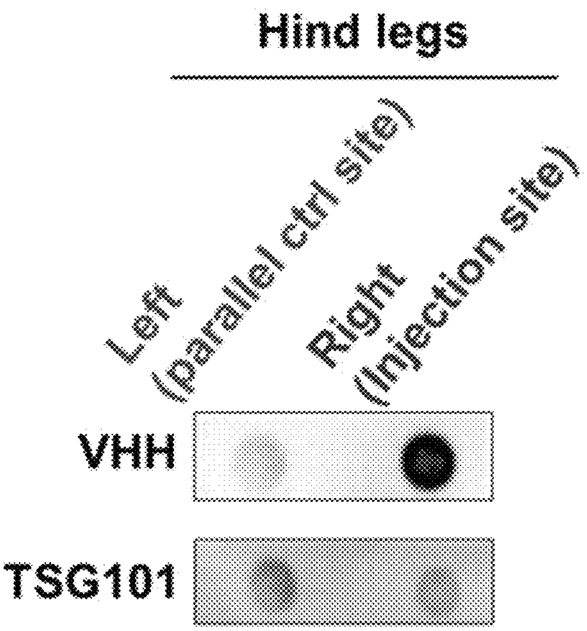
Figure 7C:
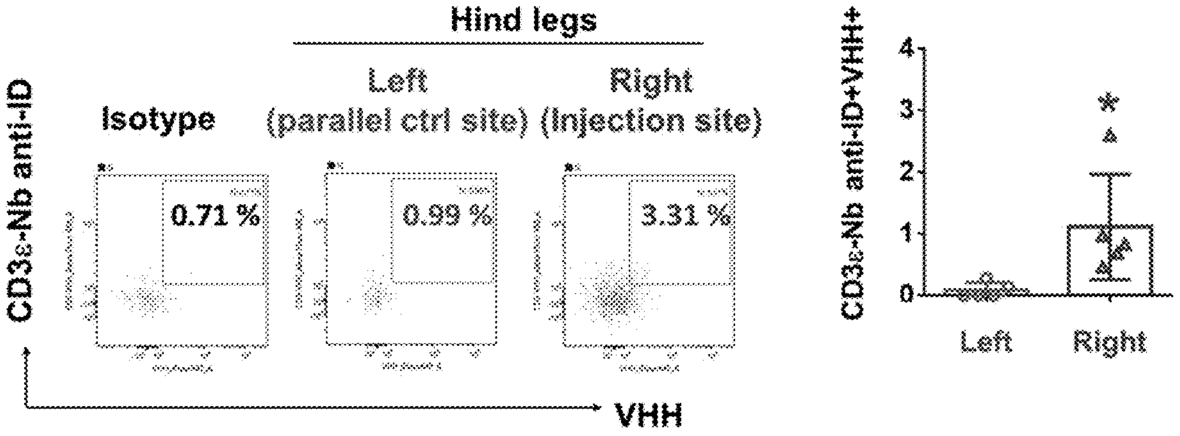
Figure 7D:
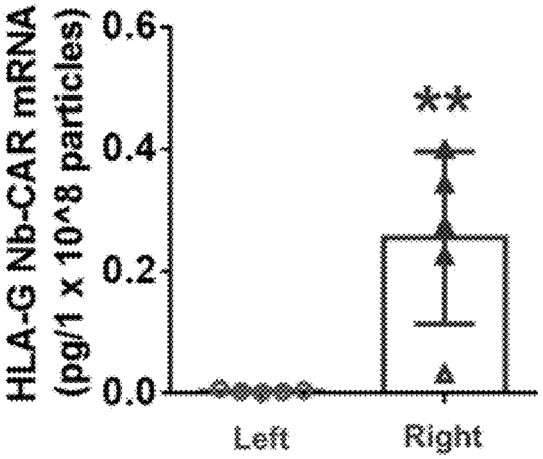

I.M. Injection of In Vivo Plasmid of Fusion Protein Induces Secretion of Fusion Protein In Vivo FIGS. 6A and 6B show in vivo generation of the fusion protein, in which the fusion protein is also called preloaded CD3ε-nanobody (Nb) extracellular vesicles (EVs) (preload CD3ε-Nb EVs). (6A) Schematic protocol for in vivo generation of preload CD3ε-Nb EVs in COLO 205 tumor-bearing PBMC-humanized NSG mice (huNSG). After 7 days of intramuscular (I.M.) injection with vehicle control or preload CD3ε-Nb EV DNA transgene (1 mg/kg) at the right hind leg, the plasma were harvested from the mice, and determined the expression levels of CD3ε Nb moieties on EV particles through flow cytometry analysis using specific antibodies against VHH and CD3ε Nb, and the defined beads for size determination (6B).

The results of this example indicate that I.M. injection of in vivo plasmid of the fusion protein induces secretion of the fusion protein in vivo.

Example 7

In Vivo Plasmid of Fusion Protein-Treated Hind Leg Capable to Secret Fusion Protein FIGS. 7A-7D show demonstration of in vivo generated the fusion protein from hind leg through intramuscular injection route, in which the fusion protein is also called preloaded CD3ε-nanobody (Nb) extracellular vesicles (EVs) (preload CD3ε-Nb EVs). (7A) After 7 days of I.M. injection with vehicle control or preload CD3ε-Nb EV DNA transgene (1 mg/kg) at the right hind leg, the mice were sacrificed and their muscle tissues of both hind legs were collected.

Subsequently, these hind leg tissues were subjected into 6-well plate supplemented with 1 ml serum-free RPMI1640 media. On the next day, the supernatants were harvested and filtrated with 0.22 μm filter membrane and 30 kDa cut-off column. Then the purified supernatants were analyzed by dot plot (7B) or flow cytometry analysis using specific antibodies against VHH and CD3ε Nb, and the defined beads for size determination (7C), or the levels of HLA-G Nb-CAR mRNA was detected by qPCR using specific Taqman primer probe (7D).

The results of this example indicate that in vivo plasmid of the fusion protein-treated hind leg is capable to secret the fusion protein.

Example 8

Figure 8A:
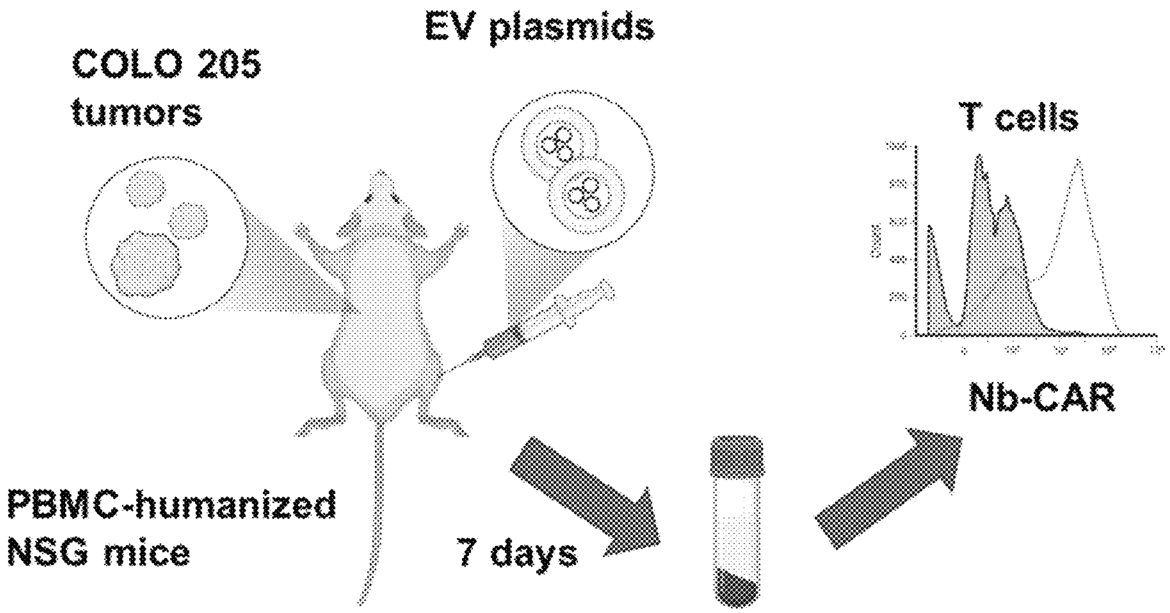
FIGS. 8A and 8B show in vivo generation of Nb-CAR-expressing T cells through I.M. injection of transgene of the fusion protein, in which the fusion protein is also called preloaded CD3ε-nanobody (Nb) extracellular vesicles (EVs) (preload CD3ε-Nb EVs). (8A) Schematic protocol for in vivo generation of Nb-CAR-expressing T cells through injection with preload CD3ε-Nb EV transgene in COLO 205 tumor-bearing PBMC-humanized NSG mice (huNSG). After 7 days of I.M. injection with vehicle control or preload CD3ε-Nb EV DNA transgene (1 mg/kg) at the right hind leg, the buffy coats were for determining the frequencies of Nb-CAR-expressing cells by flow cytometry analysis using specific antibodies against VHH and CD3 (8B).
Figure 8B:
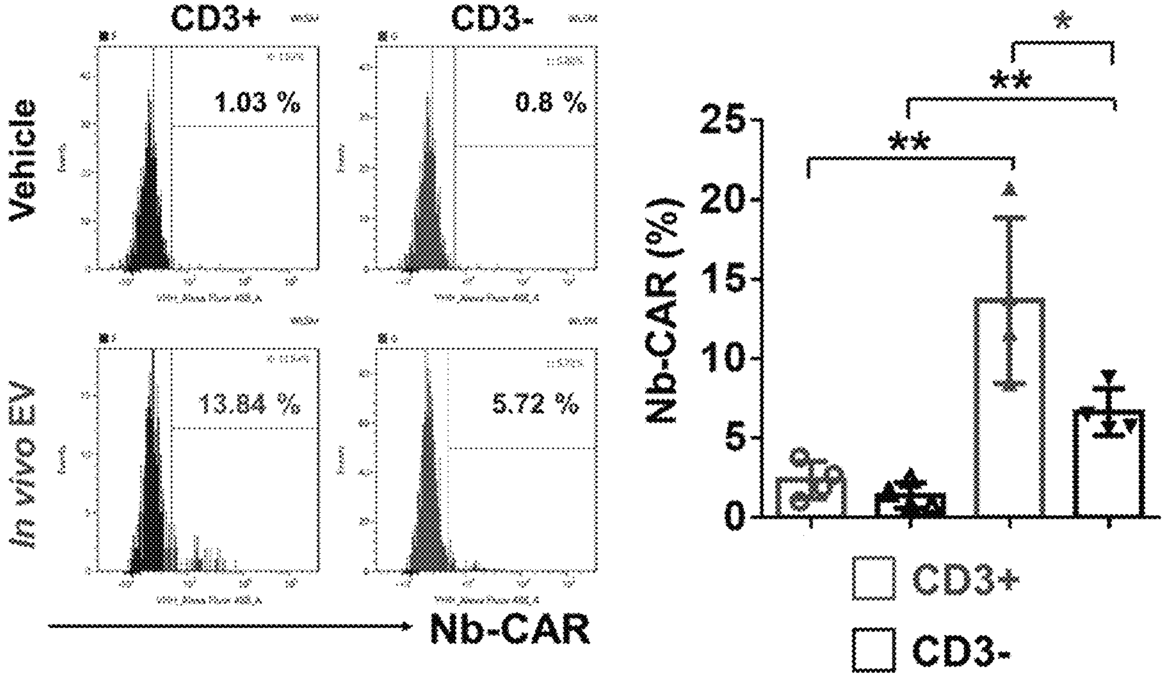
Figure 9A:
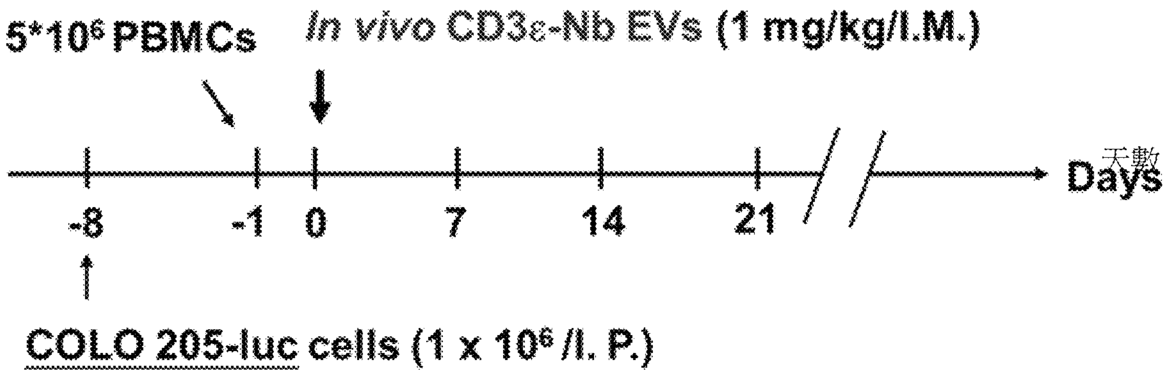
FIGS. 9A-9D show antitumor effect induced by I.M. injection of transgene of the fusion protein, in which the fusion protein is also called preloaded CD3ε-nanobody (Nb) extracellular vesicles (EVs) (preload CD3ε-Nb EVs). (9A)
Figure 9B:
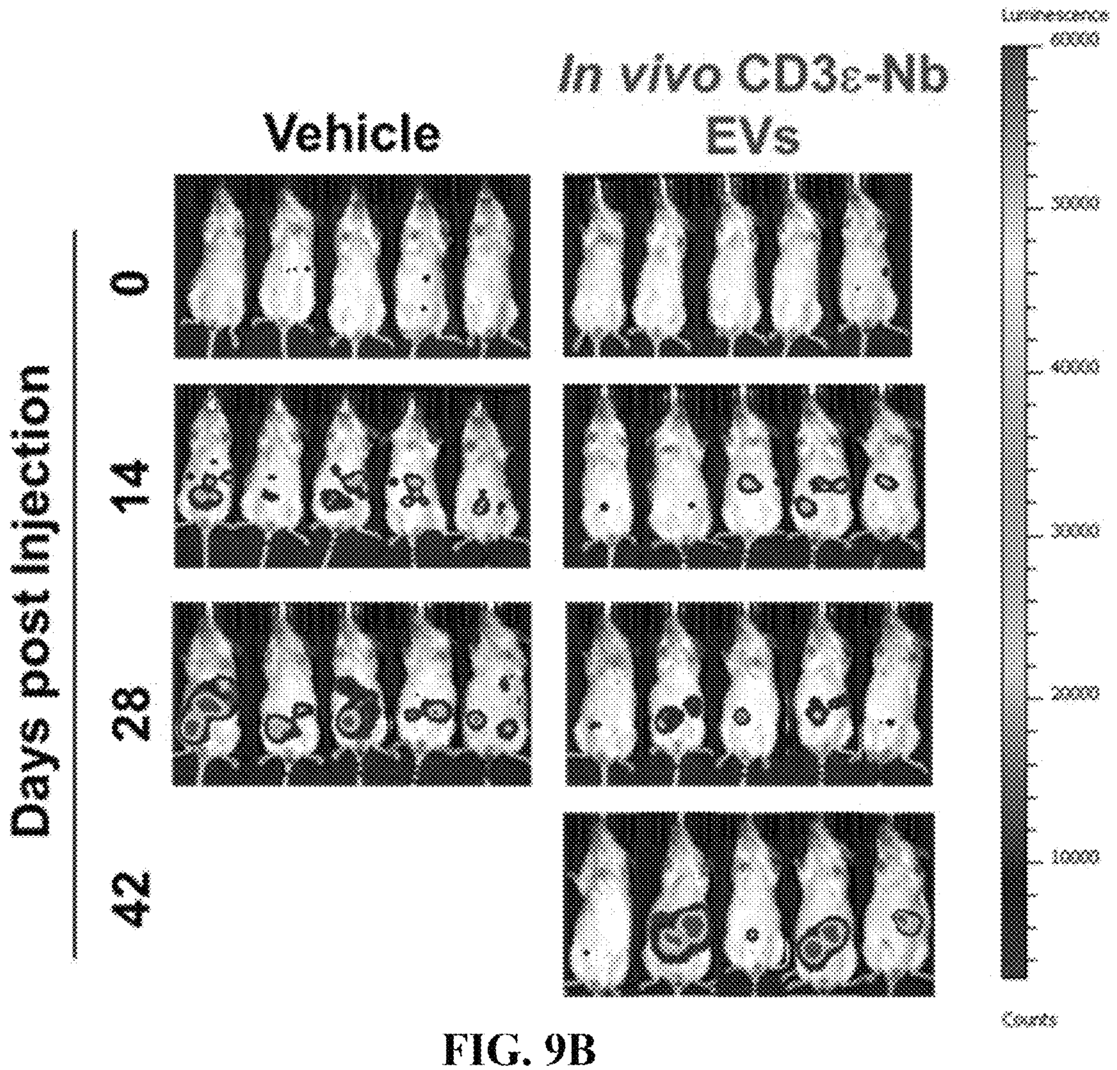
Figure 9C:
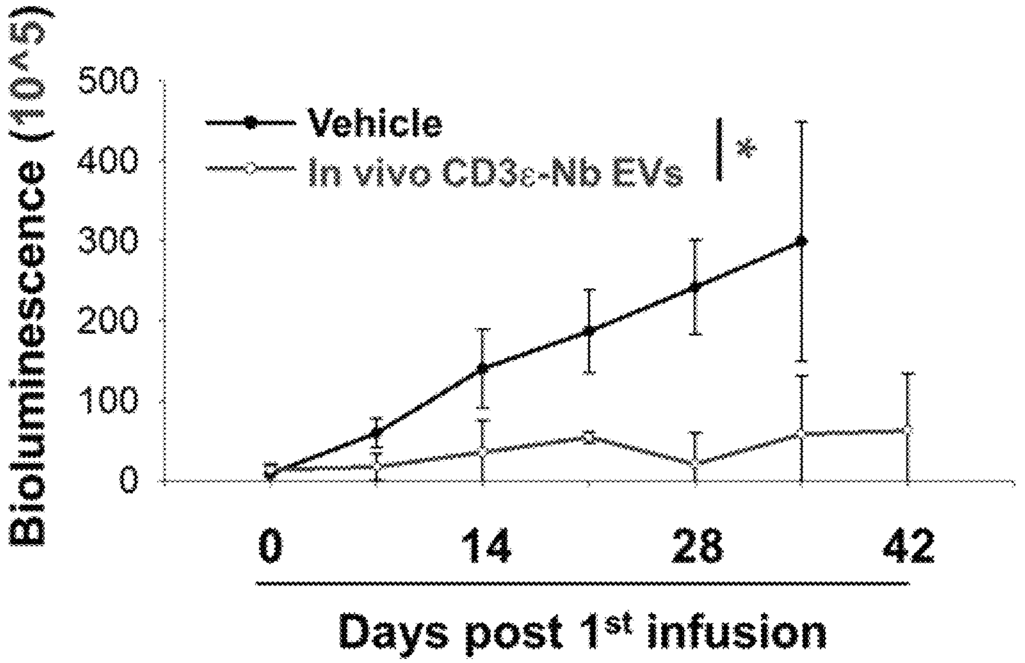
Figure 9D:
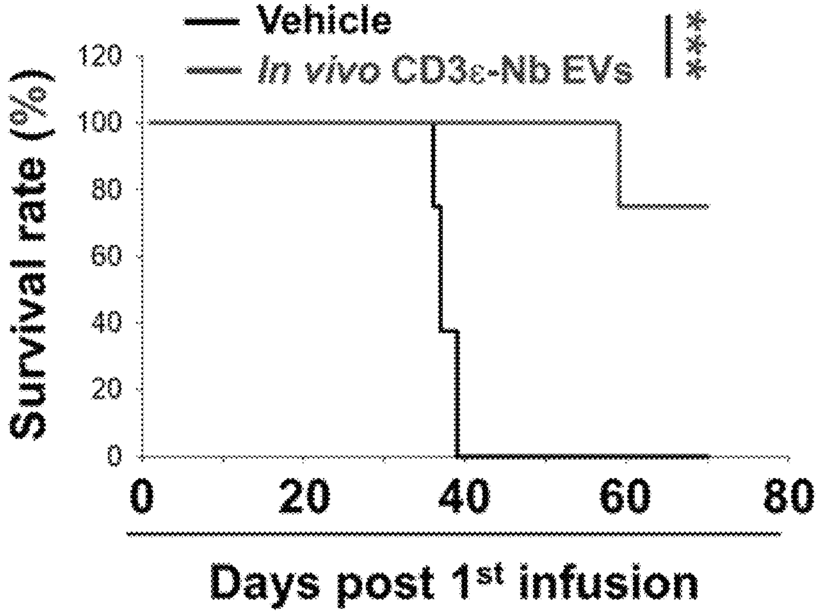

I.M. Injection of In Vivo Plasmid of Fusion Protein Increases Frequencies of Nb-CAR-Expressing Cells In Vivo FIGS. 8A and 8B show in vivo generation of Nb-CAR-expressing T cells through I.M. injection of transgene of the fusion protein, in which the fusion protein is also called preloaded CD3ε-nanobody (Nb) extracellular vesicles (EVs) (preload CD3ε-Nb EVs). (8A) Schematic protocol for in vivo generation of Nb-CAR-expressing T cells through injection with preload CD3ε-Nb EV transgene in COLO 205 tumor-bearing PBMC-humanized NSG mice (huNSG). After 7 days of I.M. injection with vehicle control or preload CD3ε-Nb EV DNA transgene (1 mg/kg) at the right hind leg, the buffy coats were for determining the frequencies of Nb-CAR-expressing cells by flow cytometry analysis using specific antibodies against VHH and CD3 (8B).

The results of this example indicate that I.M. injection of in vivo plasmid of the fusion protein increases the frequencies of Nb-CAR-expressing T cells in vivo.

Example 9

I.M. Injection of In Vivo Plasmid of Fusion Protein Enhances Anti-Tumor Activity Against Solid Tumor In Vivo FIGS. 9A-9D show antitumor effect induced by I.M. injection of transgene of the fusion protein, in which the fusion protein is also called preloaded CD3ε-nanobody (Nb) extracellular vesicles (EVs) (preload CD3ε-Nb EVs). (9A) Schematic protocol for evaluating antitumor activity of I.M. injection of preload CD3ε-Nb EV transgene in COLO 205 tumor-bearing PBMC-humanized NSG mice (huNSG). After 7 days of intraperitoneally (I.P.) implanted with COLO 205 tumor cells (1×10^6 cells), the mice were infused with 5×10^6 PBMCs through tail vein. On the next day, the mice were I.M. injected with or without preload CD3ε-Nb EV DNA transgene (1 mg/kg) at the right hind leg. The tumor growth rates were monitored by IVIS imaging system through bioluminescent channel (9B, 9C), and their survival rates were recorded (9D).

The results of this example indicate that I.M. injection of in vivo plasmid of the fusion protein enhances anti-tumor activity against solid tumor in vivo.

In summary, the fusion protein of the present invention achieves the effect of treating cancer, immunoregulation and activating immune cells through the results illustrated in the above examples.

Although the present invention has been described with reference to the preferred embodiments, it will be apparent to those skilled in the art that a variety of modifications and changes in form and detail may be made without departing from the scope of the present invention defined by the appended claims.

SEQUENCE LISTING

```
Sequence total quantity: 7
SEQ ID NO: 1            moltype = AA  length = 1393
FEATURE                 Location/Qualifiers
source                  1..1393
                        mol_type = protein
                        organism = synthetic construct
SEQUENCE: 1
MAVEGGMKCV KFLLYVLLLA FCACAVGLIA VGVGAQLVLS QTIIQGATPG SLLPVVIIAV  60
GVFLFLVAFV GCCGACKENY CLMITFAIFL SLIMLVEVAA AIAGYVFRDK VMSEFNNNFR  120
QQMENYPKNN HTAGGGGSQV QLQESGGGLV QAGGSLRLSC AASGRTFSSN VMGWFRQAPG  180
KEREFVAAIS RGSGSIYYAD SVKGRFTISR DNAKNTVYLQ MNSLKPEDTA VYYCAASRDL  240
YRYDYWGQGT QVTVSSGGGG SSILDRMQAD FKCCGAANYT DWEKIPSMSK NRVPDSCCIN  300
VTVGCGINFN EKAIHKEGCV EKIGGWLRKN VLVVAAAALG IAFVEVLGIV FACCLVKSIR  360
SGYEVMGSAA GSAMALPVTA LLLPLALLLH AARPHVQLVE SGGGSVQAGG SLKLSCVTSA  420
YTFSASGNCM GWLRQAPGKG REGIAATYTR SAKTYYADSV KGRFTISQDN AKNTVYLQMN  480
GLKPEDTATY YCAVARCAGR PDRSTLTSFA WWGQGTQVTV SSLEGGGGSG GGGSHVQLVE  540
SGGGSVQAGG SLKLSCVTSA YTFSASGNCM GWLRQAPGKG REGIAATYTR SAKTYYADSV  600
KGRFTISQDN AKNTVYLQMN GLKPEDTATY YCAVARCAGR PDRSTLTSFA WWGQGTQVTV  660
SSLEIISFFL ALTSTALLFL LFFLTLRFSV VKRGRKKLLY IFKQPFMRPV QTTQEEDGCS  720
CRFPEEEEGG CELKVFLRCI NYVFFPSLKP SSSIDEYFSE QPLKNLLLST SEEQIERCFI  780
IENISTIATV EETNQTRVKF SRSADAPAYQ QGQNQLYNEL NLGRREEYDV LDKRRGRDPE  840
MGGKPQRRKN PQEGLYNELQ KDKMAEAYSE IGMKGERRRG KGHDGLYQGL STATKDTYDA  900
LHMQYFLGRL VPRGRGAAEA ATRKQRITET ESPYQELQGQ RSDVYSDLNT QALPPRATNF  960
SLLKQAGDVE ENPGPMYRMQ LLSCIALSLA LVTNSHVQLV ESGGGLVQPG GSLRLSCAAS  1020
GFTFSSKAMS WVRQAPGKGL DWVSTINSGG GNTYYSDSVK GRFTISRDNA KNTLYLQLNS  1080
LKTEDTAMYY CSRCSDIYCG GQYTYRGQGT LVTVSSGGGG SGGGGSGGGG SEVQLVESGG  1140
GLVQPGGSLR LSCVASGFTF SSIGMSWVRQ APGKGLEWVS GLNPVGSHTG YADSVKGRFT  1200
ISRDNAKNTL HLQLNSLKTE DTAMYYCQRG YTCSGDLCER GQGTQVTVSS GGGGSGGGGS  1260
GGGGSHVQLV ESGGGSVQAG GSLRLSCTVS GVIFKNEYMG WFRQAPGKER EGVAAASPGG  1320
TITYYGDSVK GRFTISRDNA KNTVYLQMNR LKPEDTAMYY CALDPSTTSW SIIRHGPSLW  1380
RYSGRGTQVT VSS                                                     1393

SEQ ID NO: 2            moltype = AA  length = 118
FEATURE                 Location/Qualifiers
source                  1..118
```

-continued

```
                        mol_type = protein
                        organism = synthetic construct
SEQUENCE: 2
QVQLQESGGG LVQAGGSLRL SCAASGRTFS SNVMGWFRQA PGKEREFVAA ISRGSGSIYY  60
ADSVKGRFTI SRDNAKNTVY LQMNSLKPED TAVYYCAASR DLYRYDYWGQ GTQVTVSS    118

SEQ ID NO: 3            moltype = AA  length = 133
FEATURE                 Location/Qualifiers
source                  1..133
                        mol_type = protein
                        organism = synthetic construct
SEQUENCE: 3
MAVEGGMKCV KFLLYVLLLA FCACAVGLIA VGVGAQLVLS QTIIQGATPG SLLPVVIIAV  60
GVFLFLVAFV GCCGACKENY CLMITFAIFL SLIMLVEVAA AIAGYVFRDK VMSEFNNNFR  120
QQMENYPKNN HTA                                                     133

SEQ ID NO: 4            moltype = AA  length = 105
FEATURE                 Location/Qualifiers
source                  1..105
                        mol_type = protein
                        organism = synthetic construct
SEQUENCE: 4
SILDRMQADF KCCGAANYTD WEKIPSMSKN RVPDSCCINV TVGCGINFNE KAIHKEGCVE  60
KIGGWLRKNV LVVAAAALGI AFVEVLGIVF ACCLVKSIRS GYEVM                  105

SEQ ID NO: 5            moltype = AA  length = 240
FEATURE                 Location/Qualifiers
source                  1..240
                        mol_type = protein
                        organism = synthetic construct
SEQUENCE: 5
HVQLVESGGG LVQPGGSLRL SCAASGFTFS SKAMSWVRQA PGKGLDWVST INSGGGNTYY  60
SDSVKGRFTI SRDNAKNTLY LQLNSLKTED TAMYYCSRCS DIYCGGQYTY RGQGTLVTVS  120
SEVQLVESGG GLVQPGGSLR LSCVASGFTF SSIGMSWVRQ APGKGLEWVS GLNPVGSHTG  180
YADSVKGRFT ISRDNAKNTL HLQLNSLKTE DTAMYYCQRG YTCSGDLCER GQGTQVTVSS  240

SEQ ID NO: 6            moltype = RNA  length = 31
FEATURE                 Location/Qualifiers
source                  1..31
                        mol_type = other RNA
                        organism = synthetic construct
SEQUENCE: 6
ggggaggtta gggaggaggg gggtaggcgc c                                 31

SEQ ID NO: 7            moltype = AA  length = 7
FEATURE                 Location/Qualifiers
source                  1..7
                        mol_type = protein
                        organism = synthetic construct
SEQUENCE: 7
GSAAGSA                                                            7
```

What is claimed is:

1. A fusion protein, comprising an anti-CD3 single domain antibody, an exosomal protein, and an RNA binding protein, wherein the amino acid sequence of the anti-CD3 single domain antibody is a heavy chain variable domain (VHH) sequence comprising SEQ ID NO: 2, and the exosomal protein is CD63.

2. The fusion protein according to claim 1, wherein the anti-CD3 single domain antibody specifically binds to a CD3 ε.

3. The fusion protein according to claim 1, wherein the anti-CD3 single domain antibody is an anti-T cell single domain antibody.

4. The fusion protein according to claim 1, wherein the amino acid sequence of N-terminus of the CD63 is SEQ ID NO:3, and the amino acid sequence of C-terminus of the CD63 is SEQ ID NO:4.

5. The fusion protein according to claim 1, wherein the RNA binding protein is heterogeneous nuclear ribonucleoprotein (hnRNP) A2B1.

6. The fusion protein according to claim 5, wherein the hnRNP A2B1 comprises an amino acid sequence of SEQ ID NO:5.

7. The fusion protein according to claim 1, comprising an amino acid sequence of SEQ ID NO:1.

8. The fusion protein according to claim 1, further comprising an extracellular vesicle (EV) sorting motif.

9. The fusion protein according to claim 8, wherein a nucleotide sequence encoding the amino acid sequence of the EV sorting motif is SEQ ID NO:6.

10. The fusion protein according to claim 8, further comprising an HLA-G chimeric antigen receptor (CAR).

11. A pharmaceutical composition, comprising the fusion protein according to claim 1 and a pharmaceutically acceptable carrier.

12. The pharmaceutical composition according to claim 11, wherein the anti-CD3 single domain antibody specifically binds to a CD3 ε.

13. The pharmaceutical composition according to claim 11, wherein the anti-CD3 single domain antibody is an anti-T cell single domain antibody.

14. The pharmaceutical composition according to claim 11, wherein the amino acid sequence of N-terminus of the CD63 is SEQ ID NO:3, and the amino acid sequence of C-terminus of the CD63 is SEQ ID NO:4.

15. The pharmaceutical composition according to claim 11, wherein the RNA binding protein is heterogeneous nuclear ribonucleoprotein (hnRNP) A2B1.

16. A method for treating cancer, immunoregulation and activating immune cells, comprising administering to a subject in need thereof the pharmaceutical composition according to claim 11.

17. The method according to claim 16, wherein the fusion protein enhances anti-tumor activity of peripheral blood mononuclear cells (PBMCs).

18. The method according to claim 16, wherein the cancer is colorectal cancer, lung adenocarcinoma, glioblastoma, or pancreatic cancer.

* * * * *